(12) United States Patent
Di Benedetto et al.

(10) Patent No.: US 10,987,184 B2
(45) Date of Patent: Apr. 27, 2021

(54) MEDICAL OR EMERGENCY PACKAGE AND METHOD OF USE THEREOF

(71) Applicant: Drone Delivery Canada Corp., Vaughan (CA)

(72) Inventors: Paul Di Benedetto, Vaughan (CA); Gregory Colacitti, Vaughan (CA)

(73) Assignee: DRONE DELIVERY CANADA CORP., Vaughan (CA)

(*) Notice: Subject to any disclaimer, the term of this patent is extended or adjusted under 35 U.S.C. 154(b) by 252 days.

(21) Appl. No.: 15/796,210

(22) Filed: Oct. 27, 2017

(65) Prior Publication Data

US 2019/0125471 A1 May 2, 2019

(51) Int. Cl.
*A61B 50/30* (2016.01)
*A01N 1/02* (2006.01)
(Continued)

(52) U.S. Cl.
CPC ............... *A61B 50/30* (2016.02); *A01N 1/02* (2013.01); *A01N 1/0273* (2013.01);
(Continued)

(58) Field of Classification Search
CPC ............ A61B 50/00; A61B 2050/0067; A61B 2050/0076; A61B 2050/0078;
(Continued)

(56) References Cited

U.S. PATENT DOCUMENTS 5,586,438 A 12/1996 Fahy
6,210,329 B1 4/2001 Christmas et al.
(Continued)

FOREIGN PATENT DOCUMENTS

CN 204368441 U 6/2015
CN 105068486 A 11/2015
(Continued)

OTHER PUBLICATIONS

International Search Report and Written Opinion in connection to International Patent Application No. PCT/CA2018/051361, dated Jan. 22, 2019.

(Continued)

*Primary Examiner* — Ahmed M Farah
(74) *Attorney, Agent, or Firm* — Bereskin & Parr LLP/S.E.N.C.R.L., S.R.L.

(57) ABSTRACT

A portable emergency or medical package has: a body; a plurality of compartments for housing medical supplies, and a compartment for communication device, providing real time two-way communication between a user of the package and a communication appliance remote from the package, wherein the communication device is detachable from the remainder of the package. A method of delivering a package of emergency or medical supplies to a desired location provides control over the use of the medical supplies by a remote person. At the desired location, a user is instructed to remove the communication device from the package, which enables the provision of real time two-way audio communication between a remote person and the user and at least one way video communication to the remote person, whereby the remote person can provide instructions and directions to the user.

18 Claims, 5 Drawing Sheets

(51) Int. Cl.

| | | |
|---|---|---|
| *A61B 5/0205* | (2006.01) | |
| *A61F 17/00* | (2006.01) | |
| *A61B 50/00* | (2016.01) | |
| *A61N 1/39* | (2006.01) | |
| *A61B 5/021* | (2006.01) | |
| *A61B 5/024* | (2006.01) | |
| *A61B 5/08* | (2006.01) | |
| *A61B 5/145* | (2006.01) | |
| *A61M 5/00* | (2006.01) | |
| *A61M 5/20* | (2006.01) | |

(52) U.S. Cl.
CPC .......... *A61B 5/02055* (2013.01); *A61B 5/021* (2013.01); *A61B 5/024* (2013.01); *A61B 5/0816* (2013.01); *A61B 5/14542* (2013.01); *A61B 2050/0067* (2016.02); *A61B 2050/3008* (2016.02); *A61B 2562/242* (2013.01); *A61F 17/00* (2013.01); *A61M 5/002* (2013.01); *A61M 5/20* (2013.01); *A61N 1/3904* (2017.08)

(58) Field of Classification Search
CPC ............ A61B 50/30; A61B 2050/3008; A61B 2050/3009; A61B 2050/301; A61B 2050/3013; A61B 2050/31; A61B 2050/311; A61B 2050/312; A61B 2050/314; A61B 5/01; A61B 5/02; A61B 5/0205; A61B 5/02055; A61B 5/021; A61B 5/024; A61B 5/08; A61B 5/0816; A61B 5/14542; A61B 5/1455; A61M 5/00; A61M 5/002; A61M 5/003; A61M 2005/004; A61M 2005/005; A01N 1/02; A01N 1/0242; A01N 1/0263; A01N 1/0273
USPC ................ 600/301, 309, 310, 322–324, 481, 600/483–485, 529–531
See application file for complete search history.

(56) References Cited

U.S. PATENT DOCUMENTS

| | | | |
|---|---|---|---|
| 7,277,752 B2* | 10/2007 | Matos .................... | A61B 5/411 607/5 |
| 7,584,071 B2 | 9/2009 | Lee | |
| 8,106,748 B2 | 1/2012 | Lee | |
| 8,593,108 B2* | 11/2013 | Ferber .................. | H02J 7/0044 320/114 |
| 8,948,935 B1 | 2/2015 | Peeters et al. | |
| 9,051,043 B1 | 6/2015 | Peeters et al. | |
| 9,056,676 B1 | 6/2015 | Wang | |
| 9,120,568 B2 | 9/2015 | Herman et al. | |
| 9,174,733 B1 | 11/2015 | Burgess et al. | |
| 9,179,260 B2 | 11/2015 | Ostrander et al. | |
| 9,244,147 B1 | 1/2016 | Soundararajan et al. | |
| 9,302,783 B2 | 4/2016 | Wang | |
| 9,305,280 B1 | 4/2016 | Berg et al. | |
| 9,307,383 B1 | 4/2016 | Patrick | |
| 9,334,052 B2 | 5/2016 | Pasko et al. | |
| 9,357,766 B2* | 6/2016 | Steinman ............ | A01N 1/0273 |
| 9,384,668 B2 | 7/2016 | Raptopoulos et al. | |
| 9,387,928 B1 | 7/2016 | Gentry et al. | |
| 9,429,953 B1 | 8/2016 | Miller et al. | |
| 9,527,605 B1 | 12/2016 | Gentry et al. | |
| 9,573,684 B2 | 2/2017 | Kimchi et al. | |
| 9,536,216 B1 | 3/2017 | Lisso | |
| 2005/0129108 A1 | 6/2005 | Bendall et al. | |
| 2005/0154653 A1 | 7/2005 | Jongebloed | |
| 2007/0203727 A1 | 8/2007 | Moore | |
| 2009/0076368 A1 | 3/2009 | Balas | |
| 2009/0108016 A1 | 4/2009 | Brown et al. | |
| 2011/0264311 A1 | 10/2011 | Lee et al. | |
| 2012/0143482 A1 | 6/2012 | Goossen et al. | |
| 2013/0074614 A1 | 3/2013 | Holmes et al. | |
| 2014/0032034 A1 | 1/2014 | Raptopoulos et al. | |
| 2014/0061273 A1* | 3/2014 | Bullivant .................. | A45F 3/04 224/576 |
| 2014/0316243 A1 | 10/2014 | Niedermeyer | |
| 2015/0120094 A1 | 4/2015 | Kimchi | |
| 2015/0158587 A1 | 6/2015 | Patrick et al. | |
| 2015/0336669 A1 | 11/2015 | Kantor et al. | |
| 2015/0339933 A1 | 11/2015 | Batla et al. | |
| 2015/0353195 A1 | 12/2015 | Peeters et al. | |
| 2015/0370251 A1 | 12/2015 | Siegel et al. | |
| 2015/0379874 A1 | 12/2015 | Ubhi et al. | |
| 2016/0001883 A1 | 1/2016 | Sanz et al. | |
| 2016/0016664 A1 | 1/2016 | Basuni | |
| 2016/0033966 A1 | 2/2016 | Farris et al. | |
| 2016/0096622 A1 | 4/2016 | Richardson | |
| 2016/0148495 A1 | 5/2016 | Buchanan | |
| 2016/0163204 A1 | 6/2016 | Raptopoulos et al. | |
| 2016/0200438 A1 | 7/2016 | Bokeno et al. | |
| 2016/0236778 A1 | 8/2016 | Takayama et al. | |
| 2016/0244165 A1 | 8/2016 | Patrick et al. | |
| 2016/0284221 A1 | 9/2016 | Hinkle et al. | |
| 2016/0311532 A1 | 10/2016 | Fleck | |
| 2017/0203843 A1 | 7/2017 | Chan | |
| 2017/0292757 A1* | 10/2017 | Weaver ................... | A61J 1/165 |
| 2017/0369167 A1 | 12/2017 | Meadow | |

FOREIGN PATENT DOCUMENTS

| | | |
|---|---|---|
| CN | 204846372 U | 12/2015 |
| CN | 205169496 U | 4/2016 |
| DE | 102014105583 A1 | 10/2015 |
| DE | 102014213023 A1 | 1/2016 |
| WO | 2007081947 A2 | 7/2007 |
| WO | 2014089083 A1 | 6/2014 |
| WO | 2014170646 A1 | 10/2014 |
| WO | 20150618008 A1 | 4/2015 |
| WO | 2015175242 A1 | 11/2015 |
| WO | 2015168573 A1 | 2/2016 |
| WO | 2016019242 A1 | 2/2016 |
| WO | 2016037219 A1 | 3/2016 |
| WO | 2016094067 A1 | 6/2016 |

OTHER PUBLICATIONS

Dronenet the next Big thing; Global Guerrillas, Wednesday, Jan. 2, 2013.
Toor, "This startup is using drones to deliver medicine in Rwanda", http://theverge.com/1016/4/5/11367274/zipline-drone-delivery-rwanda-medicine-blood, Apr. 5, 2016.
Starr, "Ambulance drone delivers help to heart attack victims", https://www.cnet.com/news/ambulance-drone-delivery-help-to-heart-attack-victims, Oct. 28, 2014.
Written Opinion of the International Searching Authority and International Search Report in respect of PCT/ CA2018/051362 dated Jan. 16, 2019.
Boutilier, J. et al., "Optimizing a drone network to deliver automated external defibrillators". Circulation 2017—The Journal of Emergency Medicine, Sep. 30, 2017 (Sep. 30, 2017), vol. 53, Issue No. 3, pp. 445 and 446.
Dorling, K. et al., "Vehicle Routing Problems for Drone Delivery". IEEE Transactions on Systems, Man, and Cybernetics: Systems, Jan. 1, 2017 (Jan. 1, 2017), vol. 47, Issue No. 1, pp. 70 to 85.
Thiels, C. et al., "Use of Unmanned Aerial Vehicles for Medical Product Transport". Air Medical Journal, Mar. 1, 2015 (Jan. 3, 2015), vol. 34, Issue 2, pp. 104 to 108.

* cited by examiner

MEDICAL OR EMERGENCY PACKAGE AND METHOD OF USE THEREOF

FIELD

The present disclosure relates to a medical package or an emergency package or kit and related method of use, and more particularly, but not exclusively, to a package or kit that is portable.

CROSS-REFERENCE TO RELATED APPLICATION

This application is filed simultaneously with applicant's application entitled 'Unmanned aerial vehicle delivery system for delivery of medical or emergency supplies', the whole contents of which are incorporated by reference.

INTRODUCTION

The following paragraphs are not an admission that anything discussed in them is prior art or part of the knowledge of persons skilled in the art.

PCT application WO2014/089083 discloses a medicament storage, dispensing, and administration system and method. It provides a storage case that is stationary and may be provided with some communication function.

SUMMARY

This summary is intended to introduce the reader to the more detailed description that follows and not to limit or define any claimed or as yet unclaimed invention. One or more inventions may reside in any combination or subcombination of the elements or process steps disclosed in any part of this document including its claims and figures.

In accordance with a first aspect of the present disclosure, there is provided a portable emergency or medical package comprising:
 a body;
 a plurality of compartments for housing medical supplies;
 and a compartment for communication device, providing real time two-way communication between a user of the package and a communication appliance remote from the package, wherein the communication device is detachable from the remainder of the package.

In accordance with a second aspect of the present disclosure, there is provided method of delivering a package of emergency or medical supplies and providing control over the use of the medical supplies by a remote person, the method comprising:
 providing a package of medical supplies, including a communication device to be used by a user, the communication device providing for two-way audio communication and visual communication from the communication device to communication applicant between a user of the headset at an emergency scene and the remote person;
 at the desired location instructing a user at a location to remove the communication device from the package;
 providing real time two-way audio communication between a remote person and the user and at least are way visual communication to the remote person, whereby the remote person can provide instructions and directions to the user.

The emergency or medical package and method may comprise a plurality of separate modules, and the modules may be connectible in different combinations to provide different combinations of supplies.

Further, the emergency or medical package may include fasteners for the separate modules permitting the modules to be assembled in different combinations and providing for attachment of the package to another device for transporting the package.

BRIEF DESCRIPTION OF THE FIGURES

For a better understanding of the described embodiments and to show more clearly how they may be carried into effect, reference will now be made, by way of example, to the accompanying drawings in which.

DETAILED DESCRIPTION

Figure 1:
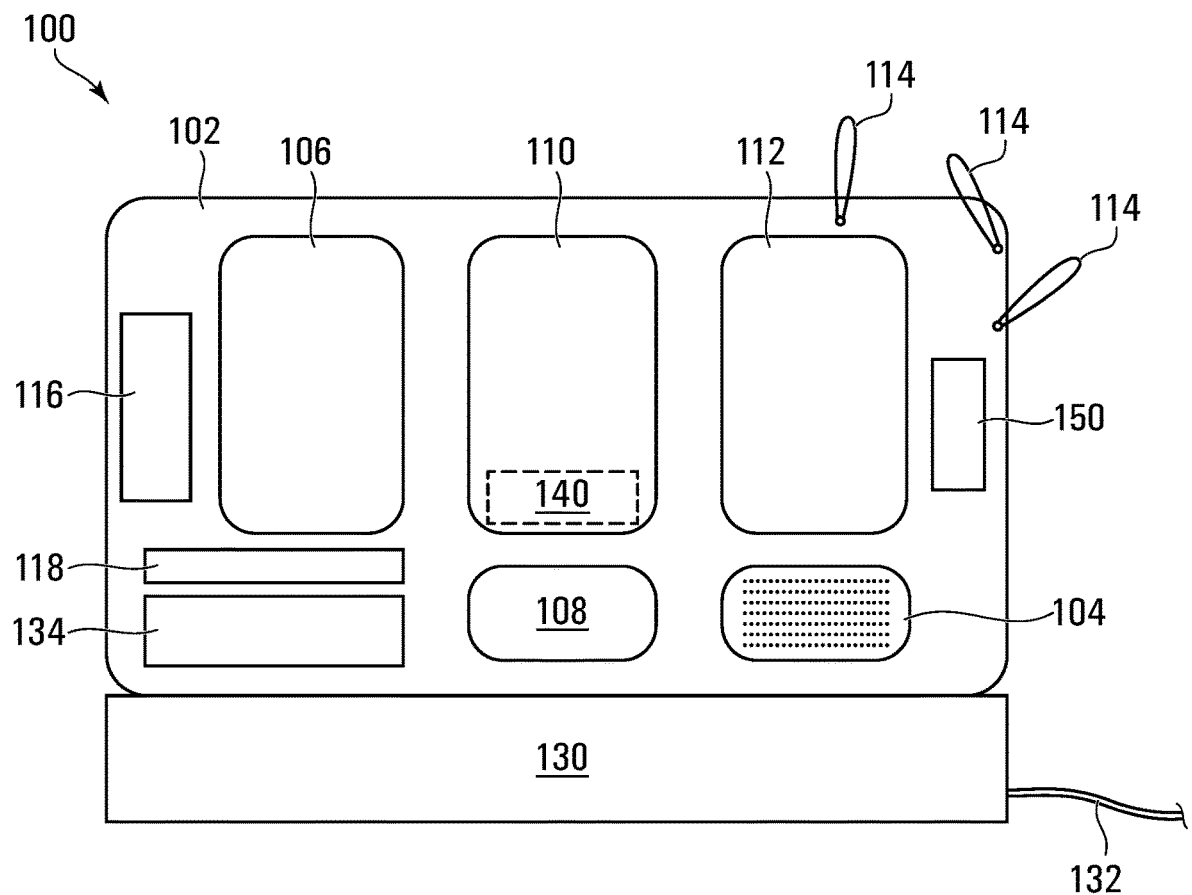
FIGS. 1 and 2 show a top view and a side view of a medical package.

Various systems, apparatuses or methods will be described below to provide an example of an embodiment of each claimed invention. No embodiment described below limits any claimed invention and any claimed invention may cover apparatuses and methods that differ from those described below. The claimed inventions are not limited to systems, apparatuses and methods having all of the features of any one apparatus or method described below, or to features common to multiple or all of the systems, apparatuses or methods described below. It is possible that a system, apparatus or method described below is not an embodiment of any claimed invention. Any invention disclosed in a system, apparatus or method described below that is not claimed in this document may be the subject matter of another protective instrument, for example, a continuing patent application, and the applicant(s), inventor(s) and/or owner(s) do not intend to abandon, disclaim or dedicate to the public any such invention by its disclosure in this document.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments generally described herein. Furthermore, this description is not to be considered as limiting the scope of the embodiments described herein in any way, but rather as merely describing the implementation of various embodiments as described.

This disclosure includes description of a method and system for delivering an emergency or medical package. The emergency or medical package may be in response to a request for assistance by first responders, and may be labelled or identified as a "first responders" package. It may otherwise be a medical package requiring prompt or emergency delivery and labelled or identified as an "Emergency package". An "Emergency package" may also include non-medical items that require emergency or rapid delivery.

The emergency package may include a communication device, for example a headset that provides for two way audio communication and at least one way video communication to a remote person. The intent may be to provide the remote person with as much sensory input as received by a user of the package. The remote person can then provide advice and instruction to a user of the package. The package and method then enable a remote person who has more medical training than the user of the package to provide advice and/or instruction to the user; for example a first responder may provide advice to an unskilled person, or a physician can provide advice to a first responder.

QR CODES AND IDENTIFIER-DEVICE. In some cases, unique identifiers may include one or more Quick Response (QR) codes. In such cases, a medical package and/or a mobile device may include a QR code reader operable to read the QR codes to extract the dataset(s) that may be embodied in the QR codes, and to communicate the dataset(s).

Figure 2:
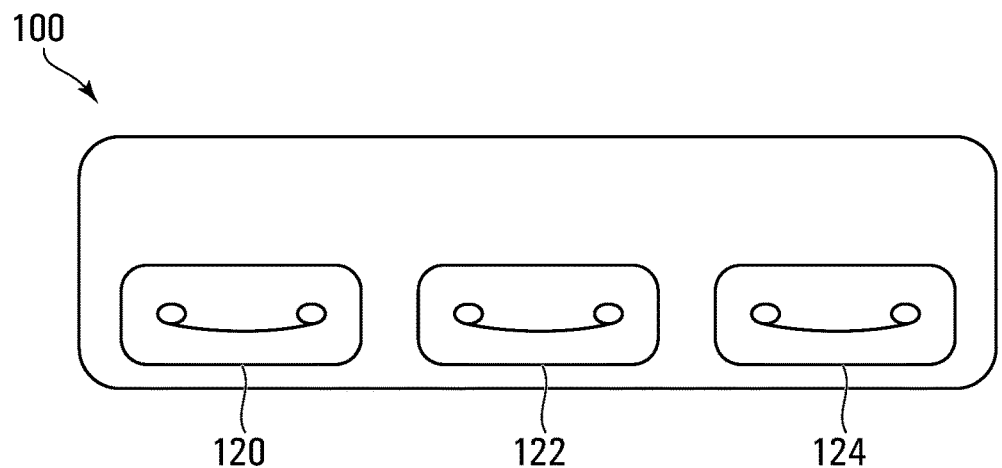

Reference is made to FIGS. 1 and 2 which show an exemplary emergency package, indicated at 100. The Package 100 may include a body 102 formed from a light but impact resistant material, for example, fiber reinforced plastic. The body 102 may be provided with a high visibility finish and may be waterproof.

The package 100 includes a speaker 104 and a display screen 106 for displaying instructions. The screen 106 may be a touchscreen, to accept input comments.

The package 100 may include a start button indicated at 108, which may be provided with a sharp contrasting colour relative to other elements, to draw users' attention to it. At 110, there is a compartment enclosing a communication device such as a headset, to be worn by a user. At 112, there is a compartment that can include an automated external defibrillator (AED). As indicated at 114, various antennas can be provided, for example for GPS communication, cellular communication and for communication to a headset contained in the compartment 110. Communication can include RFID to items in the package 100, Bluetooth, and NFC. A GPS receiver 150 is provided, so that the location of the package can be automatically identified.

A side view of the package 100 is shown in FIG. 2, indicating compartments or doors 120, 122, 124.

As indicated, sensors 116 can be provided for detecting a variety of parameters, for transmission to a control center or the like. Sensors 116 can detect, for example, temperature, presence of individual medical devices or medicines, and maybe capable of reading expiry dates for medicines and the like. For certain medicines, including blood products, it may be necessary that they be stored below a certain temperature, and for this reason, it may be required to monitor the temperature of the package 100.

For communication purposes, a communication unit 118 is provided. To power the communication unit 118, and other electronic components, e.g. the headset or communication device 140, speaker 104 and display 106, a battery 134 is provided. In a storage or standby condition, the package 100 can be connected to or mounted on a battery charger 130 provided with connected to a power source, indicated schematically at 132. Thus, in a storage or standby state, the battery 134 would be maintained at a full charge. The state of the battery 134 can be indicated on a suitable display on the package 100, and may be communicated to an external control center.

Figure 3A:
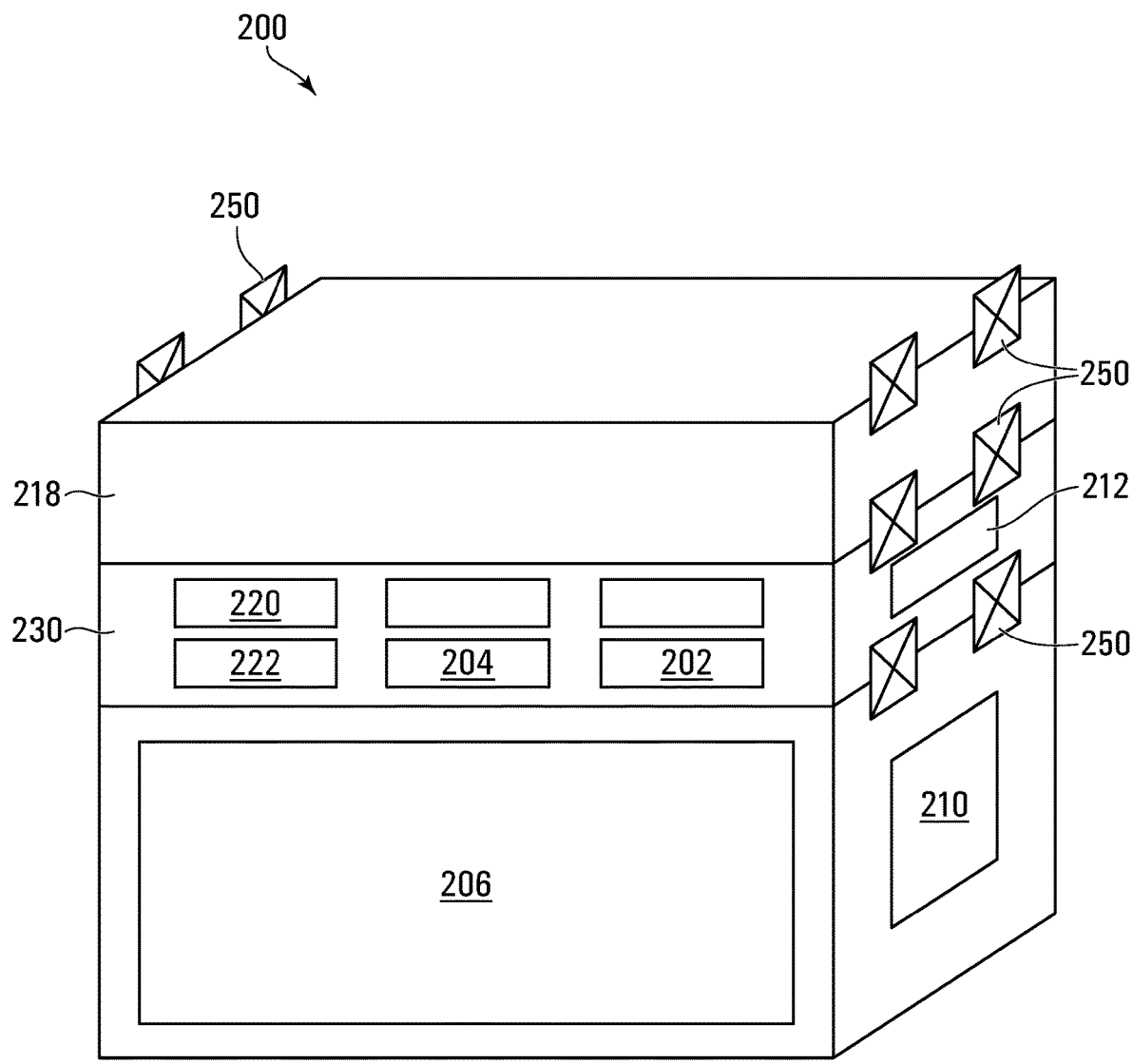
FIG. 3a shows a perspective view of a second embodiment of the medical package.
Figure 3B:
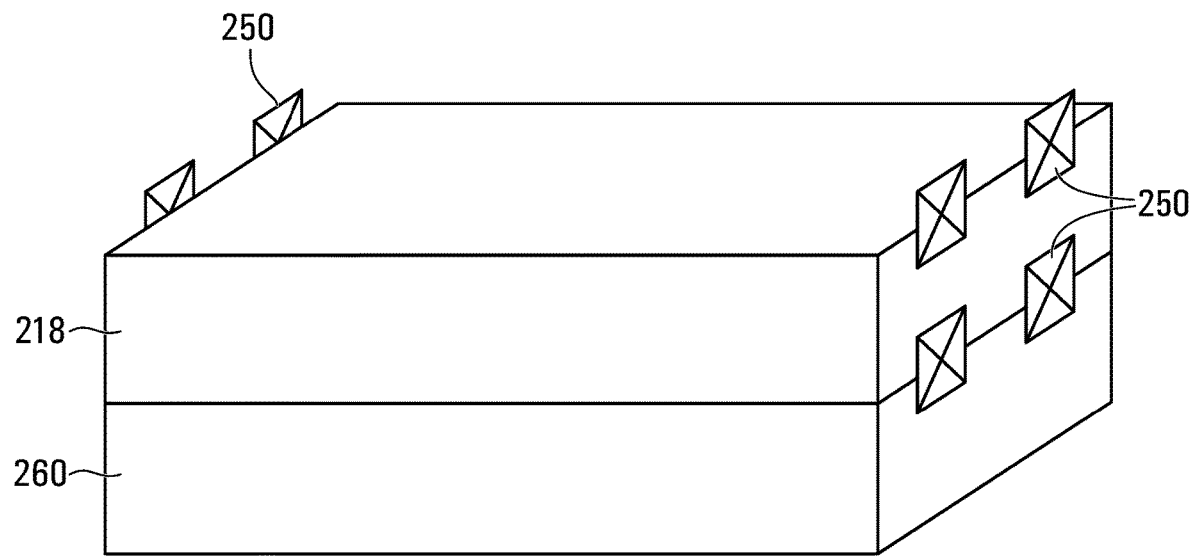
FIGS. 3b and 3c show perspective views of third and fourth embodiments of the medical package.
Figure 3C:
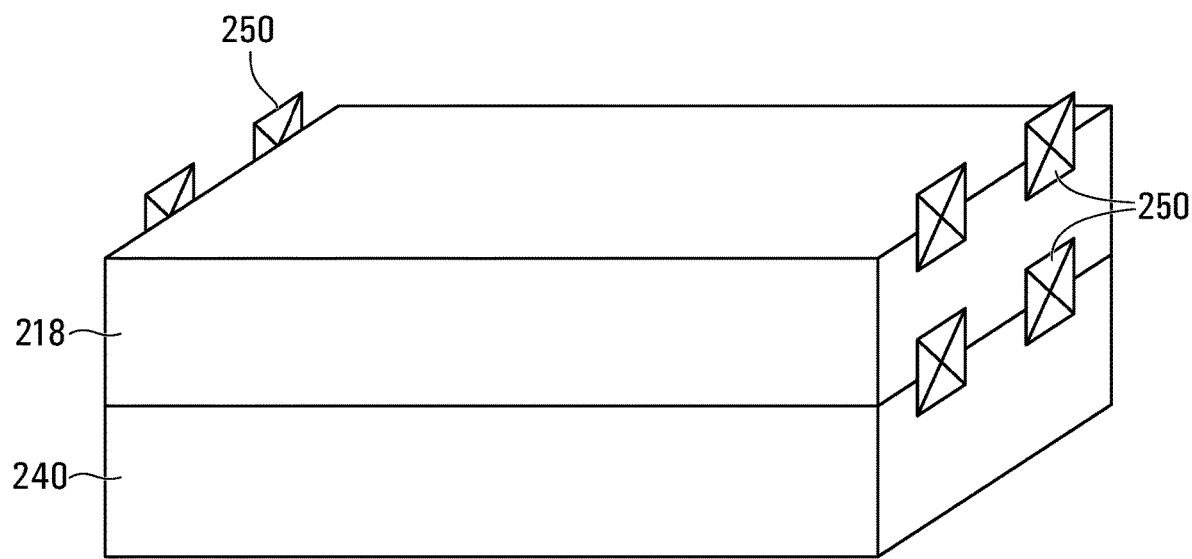

Reference is now made to FIGS. 3a, 3b and 3c, which shows further embodiments of the medical package. Like components in FIGS. 3a, 3b and 3c are given the same reference numerals as in FIG. 1, with the package as a whole indicated by the reference 200.

Here, the package 200 includes vaccines indicated at 202 which may be provided in drawers as indicated at 204, and also drawers 220, 222 and the compartment 212 for an AED as in the first embodiment. Drawers or other containment mechanisms can be provided for transport of blood, plasma, other blood components, for use with someone requiring medical attention. As required and in known manner, the package can provided with features to maintain such blood and other supplies in a required state, e.g. with refrigeration for a transfusion product. As well, provision can be made for collection of samples of blood and other body fluids from a person. In known manner, such samples can be treated to stabilize them for transport and storage. For example, blood samples may be mixed with coagulants or anti-coagulants, and may be stored and transported in a refrigerated state.

Additionally, this medical package 200 further includes an organ box 206, for transporting organs. For this purpose, the medical package 200 can be provided with device, indicated schematically at 210, for maintaining an organ in a desired state, e.g. at a desired temperature. Commonly, organs are transported in a chilled condition, (cold ischemic storage), or alternatively they may be transported and maintained at body temperature, optionally including provision to circulate blood or a blood substitute and other body fluids through the organ.

The package may be provided by a series of modules that can be assembled in desired combinations, depending upon a particular need or application. Thus, the requirement for the organ box should be known in advance and the inclusion or omission of the organ box can be determined. In the second embodiment of FIG. 3a, there is a communications unit or module 218, a drawer unit or module 230 and an organ unit or module 240, including the organ box 206 and the device 210 for controlling conditions in the organ box 206.

To enable different combinations of modules to be formed, attachment clips or fasteners 250 are provided, and these may be in the form of complementary male and female fasteners. They are also of common design and location so that different combinations of modules can be assembled, as detailed for FIGS. 3b and 3c.

Further the fasteners 250 at the top of the communication unit 218 can be used to connect the whole package 200 to another device. For example the package 200 can be connected to a carrying frame or to mounting location in a vehicle. For delivery by a UAV, the fasteners 250 can be used to mount the package, detachably to the UAV (not shown). Alternatively, the package can simply be inserted into a compartment of a UAV or other vehicle, which compartment may have a door to close off the compartment to ensure the package 200 is secure. The fasteners may also be used to attach a package to the frame of a backpack or the like so that a first responder can deliver the package on foot, or to a simple carrying frame.

FIGS. 3b and 3c show alternative configurations of the package. As indicated in FIG. 3b, the package could include just the communication unit 218 and a module or unit 260 for an AED, while in FIG. 3c the package includes the communication unit 218 and the organ unit or module 240. Thus, the concept is to include only those units needed for a particular application, to keep weight to a minimum. This may be advantageous for certain applications, e.g. where the package is to be delivered by air where weight is usually a factor. More particularly, for delivery by UAV, keeping weight down may be advantageous and may give shorter flight or delivery times and/or faster delivery of a package.

It is anticipated that the medical package may be made available at a wide variety of locations, including certain first responder locations, such as ambulance locations, fire halls, and also public buildings, e.g. town halls, community centers, libraries, etc., where first responders and other medical personnel may not be immediately available.

The video display 106 may be an electronic display capable of showing video or images. For example, display 106 may be a liquid crystal display (LCD) or other computer monitor. The display 106 may display instructions or other information to a user such as video, images, and/or text demonstrating proper medication administration and/or emergency care. For example, the remote person may display images in a sequence once the operator has verified that a step associated with a currently-displayed image has been properly performed, may display a video that the operator has identified as relevant to a particular situation.

The package 100 may also include an additional input device such as a keyboard, keypad, mouse, and/or other known input devices. For example, an authorized user may enter a security code for accessing the package 100 or receiving information. For certain applications and to provide additional security, a card reader e.g. a magnetic stripe reader for reading information from a card can be included. For example authorized users may be issued a card providing access to the package 100.

Figure 4:
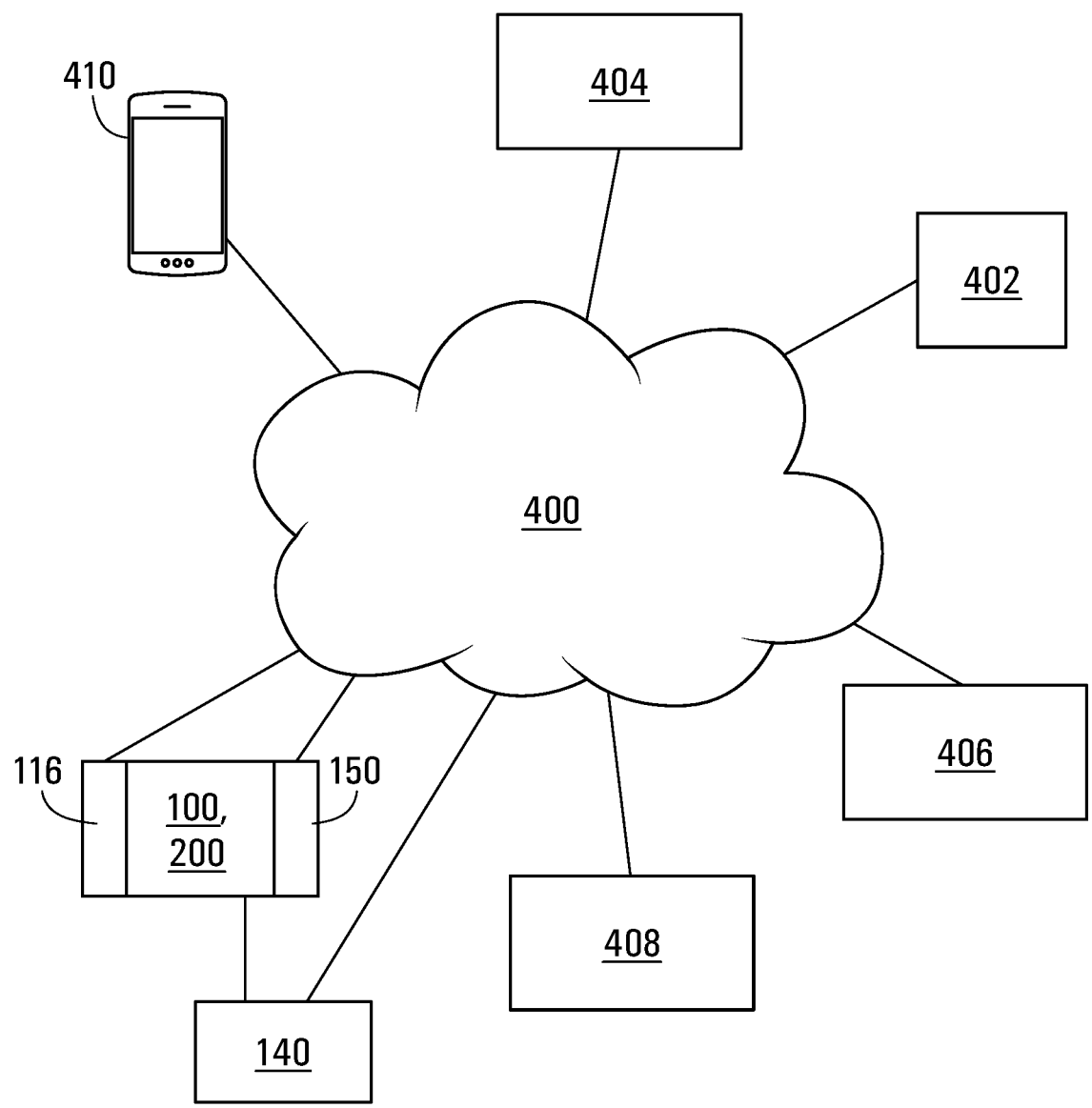
FIG. 4 shows schematically network communications.

FIG. 4, shows, schematically, a network, for use with a medical package 100 or 200 of the present invention. The communication network is indicated at 400, with various users of the network indicated around the network 400.

Thus, the medical package 100 or 200 is connected wirelessly to the network 400. As indicated sensors 116 and the GPS receiver at 150 are also connected to the network 400, this connection may be independent of the communication unit 118 or through the communication unit 118. The headset or communication device 140 is shown as connected to the medical package 100, 200, and, similarly, may communicate with the network 400 through the communication unit 118 or directly.

A control center 402 is connected, wirelessly or otherwise to the network 400. Similarly, emergency service 404, first responders 406 and physicians and medical specialists 408 are also connected, again either wirelessly or otherwise to the network 400. Physicians and medical specialists are expected to be located at locations separate from the first responders 406. At least one of the control center 402, the emergency service 404, the first responders 406 and the physicians and medical specialists 408 may be provided with a communication appliance or device for communicating with the package 100, 200.

A mobile device is indicated at 410 connected to the network 400. The mobile device, and there may be multiple mobile devices, may be used by a user of a medical package 100, 200, to provide an additional communication appliance for the communication between the user and a first responder, physician, etc.

The network 400, in known manner, can include conventional telephone networks, satellite communications, communications through mobile telephone base stations and the like. It would also include a connection to GPS satellites.

The mobile device 410 may be a device such as a smartphone, tablet computer, laptop, or any other computing device, including a communication function. Commonly, the computer device will include capability for both two-way audio and visual communications.

The mobile device 410 can communicate via the network 400, and may have the ability to communicate with the package 100 using RFID, NFC or other communication. Security provisions can be included, to ensure that only approved mobile devices 410 can communicate directly with the medical package 100, 200. The mobile device 410 can include transmission of GPS (Global Positioning System) information or data, to provide the location of a user.

The control center 402 can include capability to communicate directly with the medical package 100, 200, particularly when the medical package 100, 200 is in a stored or standby state, for the control center 402 to monitor the state of the package. For example, control center 402 can monitor expiry dates of medicines and the like in medical packages distributed at a number of locations, monitor temperatures, to ensure that the medicines are stored at an acceptable conditions, and ensure that all contents of medical packages are present. When necessary action can be taken to replenish supplies of individual package, to ensure that they are complete.

For certain applications and where possible, a check may be made as to whether any specialized combination of supplies is required. Here, it is expected that, to keep the weight of the package reasonable and as detailed above, it may be provided with only supplies anticipated as being necessary for the immediate emergency situation. For example, if the indication is that a person has suffered a heart attack, then an AED (automated external defibrillator) can be provided; if the indication is that a person is suffering a severe allergic reaction, then an appropriate drug can be included. The emergency package can also be provided with standard supplies. If a specialized package is required, then the appropriate supplies are provided to the package, and as detailed below, this may require particular supplies to be provided in particular compartments.

External wireless devices may include devices such as smart phones or other portable electronics. External wireless devices may include applications for monitoring medicament usage or providing access to package 100. The package 100 may provide information to an external wireless device via a wireless reader (not shown). The package 100 includes additional components such as a processor, memory, and/or data storage device, which may be integral with the communications device 118 and/or the GPS receiver 150. Alternatively, such components may be included as part of and/or shared between those components that are illustrated.

Sensors may provide monitoring of medicines and medical devices. Each medicine may be equipped with a sensor 116. The sensor 116 may be integrated into a locks for doors for the compartments 120, 122, 124. Sensors may detect removal of the corresponding medicine and provide an indication to the communication unit 118. The communication unit 118 may report the removal of individual medicines to the control center 402. The sensors 116 may comprise a wireless reader that may periodically check wireless tags attached to the medicines to collect information.

The GPS receiver 150 may determine a physical location of medical package 100. The GPS receiver 150 may receive signals from GPS satellites in order to calculate a location of medical package 100. The GPS receiver 150 may include a memory for storing a location such no continuous communication with GPS satellites is needed.

Figure 5:
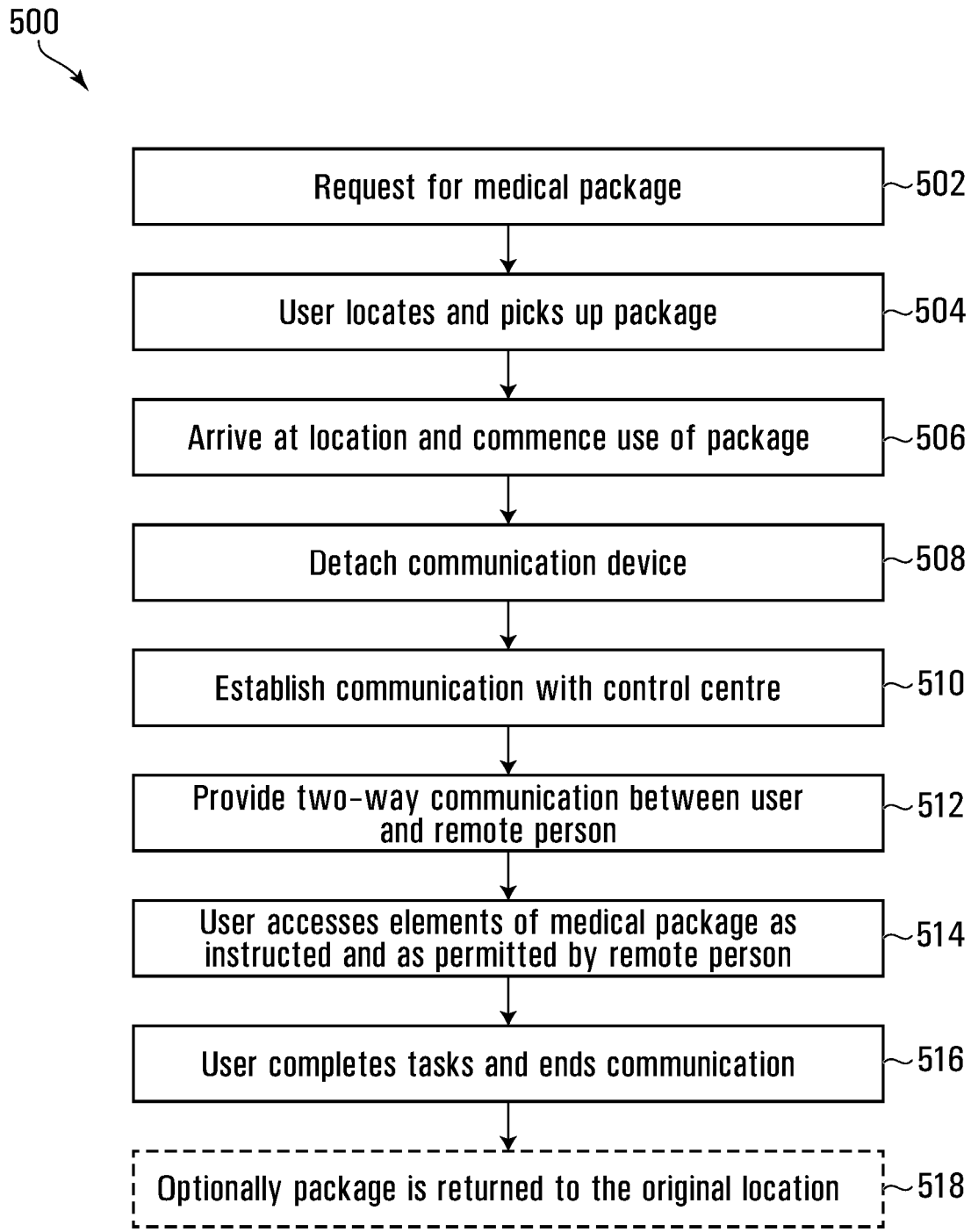
FIG. 5 is a flow chart showing steps in use of the medical package.

Referring to FIG. 5, is shown a flow chart for operation and use of the package 100, the flow chart being indicated at 500.

As indicated in 502, a request is received for the package 100. This may be communicated by someone externally, or by a person at a scene of a medical emergency or other incident, which is then a desired location for the package, who recognizes that the package is needed. That person may then locate and pick up the package as indicated at 504, or instruct or request another person to pick up and deliver the package. For example a person at the desired location or scene may contact first responders, e.g. by calling 911 or other emergency number, and a first responder will then be the person delivering and using the package, to provide attention to a person requiring attention.

At 506, a user at the scene commences to use the medical package 100. It is anticipated that in many instances, the package 100 will be delivered or available at the scene of an accident or other location where the package is required, where it may be used by an untrained, lay person with no medical or other skills, or by a first responder with limited training skills, to provide medical resources to a person requiring attention. Accordingly, the package 100 may be designed with this in mind, and, as detailed below, may provide for a trained and qualified first responder, or other medical personnel at a location remote from location or the accident scene to have varying degrees of control and input on actions taken at the emergency scene.

In general, it is anticipated that the actual user of the package 100 will be instructed or advised by a remote person with more skills or training. E.g., a first responder may be the user of the package, with instruction or advice from the physician or the medical specialist, or a remote first responder may give instruction, etc. to an untrained user.

Further, video input can be provided to the user of the medical package 100. This can either be through the video screen 106, or through the screen of a separate mobile device. The video supplied may be instructional text or demonstration video, for example. This provides two-way communication as indicated at 512.

First, the package 100 includes the start button 108. A user will press this button, and this will open the compartment 110. This action will cause the user to be provided with audio instructions, either automatically or from a remote person, e.g. a first responder, to remove a communication device, e.g. a headset 140 from the compartment 110 and place the headset on the user's head, as indicated at 508.

The headset can include both earpieces for the user and a microphone so the user has two-way voice communication with a remote person; the microphone, or additional microphone(s) can be provided to pick up all ambient audio. The headset may also include a camera, so a remote person, e.g. a first responder, will have essentially the same eye view of the emergency scene as the user. The intent is to provide the remote, first responder with the same audio and visual information as the user at the scene of the accident or emergency, who is providing medical resources or attention to a person requiring attention. Thus, the user establishes communication with a remote person, as indicated at 510.

It is also possible that the remote person, the, first responder could be given control over operation of the camera, to at least some degree. For example, if the camera has a zoom function, the remote first responder can control the zoom so as to obtain a view useful to that first responder.

It is also possible that other equipment could be provided, while recognizing that, in many emergency situations simplicity and quick response will be essential. For example, a second camera could be provided on a tripod or a stand, for a user to position close to an accident scene to provide a view point useful to a first responder or remote person, without movement imparted by a camera mounted on a headset.

The compartment 110, or a separate compartment, may also include equipment for measuring vital signs of a person requiring attention, who may be injured or who may have had a medical incident, such as a stroke or heart attack, requiring prompt attention. The person requiring attention may be suffering from an overdose of one or more drugs and/or alcohol. If so, the compartment may also include written instructions for use of this equipment. Additionally, the remote person can provide audio instructions to a user, for attaching the vital signs measuring equipment to an the person requiring attention. In known manner, the vital sign measuring equipment may measure blood pressure, pulse, and temperature at least. Vital signs usually also include respiratory rate, and a user at the scene may be instructed by the remote, first responder to measure the respiratory rate, e.g. by simply counting number of breaths in a certain time period; for this purpose, if necessary, the equipment can include a simple timing device or stop watch.

Thus, the step includes attaching the vital signs measuring equipment to the person requiring attention. Further, the vital signs measuring equipment can be connected to the package 100, wirelessly or otherwise, to transmit data back to a remote first responder or other person. It is recognized that in some situations, the treatment needed for the person requiring attention will be immediately apparent, even to an untrained person. Alternatively, recognizing that it will take a finite time, to deliver the emergency package, a user attending an that person may already have been in contact with a first responder by a telephone or otherwise, and, between them, it may have been determined what action is immediately required. For example, if that has a severe cut and bleeding that immediately requires that the application of a tourniquet, then it is not necessary to take time making any other assessment. Similar consideration applies, if it is immediately apparent that a person is having a heart attack; in this case, immediate application of the AED is required, and further evaluation will not be required.

In other situations, some assessment may be required, and it may often be necessary for a remote first responder or other person to gather as much information as possible, to make a determination on treatment to be applied.

For this purpose, the first responder or other person can provide instructions to a user at the scene, either through the audio link, or by text or otherwise on the video screen. Simultaneously, the user at the scene can, also using the audio link, text or otherwise, communicate back to the first responder. Where vital signs measuring equipment has been used, this can provide data directly back to the first responder. The user at the scene can also provide further information on the condition of the injured person, e.g. state of consciousness, respiratory rate, indications of bruising, and obvious external indications of injuries. A user at the scene may also be able to obtain useful information from the person requiring attention, if the person is conscious, concerning, for example, drugs, alcohol, etc. that the person has consumed. Based on this information, the first responder can determine the necessary course of action and treatment. For this purpose, the compartments 120, 122 and 124 may be locked and access controlled by the first responder or other person, as indicated at 514. Having determined a desired action or treatment, the first responder can unlock or permit access to the appropriate compartment.

For example, if an injured person is suffering an allergic reaction, access can be provided to a compartment containing an epinephrine autoinjector. Alternatively, if it is apparent that the injured person is suffering a heart attack, access to the AED is enabled; if it is apparent or determined that the person is suffering from a stroke, access to a compartment containing a clot dissolving drug can be provided.

One or more of the compartments can be provided with substances for countering the effects of overdoses of various drugs. For example to address an overdose of Fentanyl, naloxone or another antidote can be provided in the package, for use by the user of the package.

At 516, if the emergency has been resolved or the user of the scene has provided whatever treatment is possible using the first responders' emergency package, then no further action is taken. Alternatively, the sequence may end, when first responders are able to attend directly at the scene of the emergency.

Desirably, although it is recognized this may not occur in all instances, at 518, a user repacks the equipment into the package 100, and returns it to its original location.

For some applications, the location where the medical package is required may be readily determined and communicated; e.g. for an accident scene on a highway, the location can readily be communicated to a person who is to retrieve and deliver the medical package (and as required assemble the required components together). For other applications, this may not be so straightforward. For example if an accident happens in a remote area in a park away from any mapped roads and trails, it will be more difficult to communicate the location to first responders and the like. For this purpose, GPS beacons can be used. E.g. in parks and other areas, which are remote and have relatively high traffic levels, emergency buttons or beacons can be provided at regular intervals and locations, which may have wired or wireless communication to first responders. Each such emergency button may be part of a device that provides for two way communication. When activated a user or caller will be connected to a first responder, who will be provided with the exact coordinates of the beacon, and who can talk the caller to determine what medical supplies need to be sent.

Further, in many cases, where there is communication and coverage for mobile telephones, it may be possible for someone needing assistance and the medical package to call using a smart phone (or other device providing GPS location information) to first responders, who can then use GPS capabilities of the smart phone to determine that caller's location and, similarly to the other example, can discuss and determine what medical supplies are needed and how to transport them to the caller's location. It is also possible that a person can activate an app on a smart phone, to enable GPS location and transmission of emergency or SOS calls.

The Medicines provided may include one or more for treating emergency or other medical conditions. The medicines may be auto-injectors for administering a dose of epinephrine. Other suitable medicines include, but are not limited to, adrenergic agonists, antihistamines (e.g. diphenhydramine, hydroxyzine); H2 receptor antagonists (e.g. cimetidine, ranitidine, and famotidine), bronchodilators (e.g. albuterol), corticosteroids (e.g. prednisone), positive inotropic agents (e.g. glucagon and insulin), opioid antagonists (e.g. naloxone), and others for use in emergency conditions (e.g. N-acetylcysteine). As noted, the medicines provided may also include antidotes for drugs that are commonly abused and which result in users of the drugs overdosing.

While the above description provides examples of one or more apparatuses or methods, it will be appreciated that other apparatuses or methods may be within the scope of the accompanying claims. Additionally, while certain combinations of features, elements and method steps are claimed in the accompanying claims, it is to be understood that any practical combination of these features, elements and method steps is envisaged and is part of the present disclosure.

The invention claimed is:

1. A portable emergency or medical package comprising:
    a body;
    a plurality of first compartments for housing medical supplies; a communication device providing real time two-way communication between a user of the package and a communication appliance remote from the package, wherein the communication device is detachable from the remainder of the package; and
    a plurality of second, locked compartments that can be unlocked individually by a signal from the communication appliance, to enable a remote person at the remote communication appliance to open a selected second, locked compartment to permit access to the medical equipment contained therein;
    wherein the communication device comprises a headset wearable by a user and providing for two way audio communication through the communication appliance to the remote person and the headset including a camera providing visual information to the remote person.

2. A package as claimed in claim 1, wherein the communication device communicates wirelessly with the package, and the package includes wireless communication device that communicates, directly or indirectly, with the remote communication appliance.

3. A package as claimed in claim 1, wherein the package additionally includes vital signs measuring equipment for measuring at least one of a person's pulse, blood pressure and temperature, and for transmitting data from those measurements to the remote person.

4. A package as claimed in claim 3, wherein the vital signs measuring equipment communicates with the package.

5. A package as claimed in claim 4, wherein the vital signs measuring equipment additionally include sensors for measuring respiration rate and an blood oximeter measuring blood oxygen levels.

6. A package as claimed in claim 1, wherein the plurality of second, locked compartments, are provided with at least one of:
    an automated external defibrillator;
    an epinephrine autoinjector;
    an antidote for a drug; and
    A clot-dissolving drug.

7. A package as claimed in claim 1, including a battery for powering electronic components of the package.

8. A package as claimed in claim 7, including a charging facility, for charging the battery when the emergency package is in a stand-by state.

9. A package as claimed in claim 1, including a GPS receiver.

10. A package as claimed in claim 1, including vaccines.

11. A package as claimed in claim 1, including provision for transporting a human organ, blood, plasma or other body fluids, including one or both of supply to a user and collection of samples from a user.

12. A package as claimed in claim 11, including means to maintain an organ or blood component chilled or at human body temperature.

13. A package as claimed in claim 12, including a sensor for monitoring temperature of the package.

14. A package as claimed in claim 1, including a video screen, that optionally is a touch screen, for providing visual communication to a user of the package.

15. A package as claimed in claim 1, wherein the package comprises a plurality of separate modules, and wherein the modules can be connected in different combinations to provide different combinations of supplies.

16. A package as claimed in claim 1, wherein the communication device and instructions for use of the communication device are provided in a one of the first compartments of the package, and the package includes a start button, whereby the user initiates use of the package by actuating the start button, actuation of the start button causing the one first compartment containing the communication device to open to present the headset to the user and the instructions to the user.

17. A package as claimed in claim 1, wherein the camera on the headset is provided with adjustable functions, including at least a zoom function, remotely operable by the remote person.

18. A portable emergency or medical package comprising:
a body;
a plurality of first compartments for housing medical supplies;
a communication device providing real time two-way communication between a user of the package and a communication appliance remote from the package, wherein the communication device is detachable from the remainder of the package; and
a plurality of second, locked compartments that can be unlocked individually by a signal from the communication appliance, to enable a remote person at the remote communication appliance to open a selected locked compartment to permit access to the medical equipment contained therein;
wherein the communication device comprises a headset wearable by a user and providing for two way audio communication through the communication appliance to the remote person and the headset including a camera providing visual information to the remote person; and
wherein the package comprises a plurality of separate modules, the modules can be connected in different combinations to provide different combinations of supplies, and the package includes fasteners for the separate modules permitting the modules to be assembled in different combinations and providing for attachment of the package to another device for transporting the package.

* * * * *

UNITED STATES PATENT AND TRADEMARK OFFICE
CERTIFICATE OF CORRECTION

PATENT NO. : 10,987,184 B2
APPLICATION NO. : 15/796210
DATED : April 27, 2021
INVENTOR(S) : Di Benedetto et al.

Page 1 of 1

It is certified that error appears in the above-identified patent and that said Letters Patent is hereby corrected as shown below:

In the Claims

Claim 2, Column 10, Line 30, "wireless communication device" should read "a wireless communication device"

Signed and Sealed this
Third Day of August, 2021

Drew Hirshfeld
*Performing the Functions and Duties of the
Under Secretary of Commerce for Intellectual Property and
Director of the United States Patent and Trademark Office*